United States Patent [19]

Masakazu et al.

[11] Patent Number: 4,705,750

[45] Date of Patent: Nov. 10, 1987

[54] PROMOTER PLASMID CONTAINING THE PROMOTER AND USE THEREOF IN TRANSFORMING BACILLUS

[75] Inventors: Kikuchi Masakazu, Toyono; Nakahama Kazuo, Nagaokakyo, both of Japan

[73] Assignee: Takeda Chemical Industries, Ltd., Osaka, Japan

[21] Appl. No.: 683,203

[22] Filed: Dec. 18, 1984

[30] Foreign Application Priority Data

Dec. 26, 1983 [JP] Japan ................................ 58-248645

[51] Int. Cl.[4] ........................ C12P 21/00; C12N 1/20; C12N 15/00; C12N 1/00
[52] U.S. Cl. ........................................ 435/68; 435/70; 435/172.3; 435/253; 435/317; 536/27; 935/29; 935/38; 935/41; 935/74
[58] Field of Search ................ 435/68, 70, 172.3, 317, 435/839, 253; 935/22, 23, 27, 41, 74; 536/27

[56] References Cited

U.S. PATENT DOCUMENTS

| | | |
|---|---|---|
| 4,190,495 | 2/1980 | Curtiss, III . |
| 4,342,832 | 8/1982 | Goeddel et al. ................ 435/172.3 |
| 4,418,149 | 11/1983 | Ptashne et al. .................... 435/172.3 |
| 4,559,300 | 12/1985 | Kovacevic et al. .................. 435/68 |
| 4,585,739 | 4/1986 | Lovett et al. ........................ 435/253 |
| 4,626,510 | 12/1986 | Grandi ................................ 435/317 |

FOREIGN PATENT DOCUMENTS

| | | |
|---|---|---|
| 0036259 | 9/1981 | European Pat. Off. . |
| 0063494 | 10/1982 | European Pat. Off. . |
| 59-55897 | 3/1984 | Japan . |

OTHER PUBLICATIONS

Williams, D. et al. 1981, J. Bact. 146:1162.
Moran et al. (1982) *Molecular and General Genetics* vol. 186 pp. 339–346.
Devos, R. et al. 1982, NAR 10:2487.
Devos, R. et al. 1983, NAR 11:4307.
Band, L. et al. 1983, Gene 26:313.
Zukowski, M. et al. 1983, PNAS 80:1101.
Nakahama, K. et al. 1985, Gene 36:179.
Jay, G. et al. 1981, PNAS 78:5543.
Nature 293, 481 (1981).
Gene 16, 199 (1981).
Gene 22, 47 (1983).
Proceedings of the IVth International Symposium on Genetics of Industrial Microorganisms, p. 227 (1982).
Methods in Enzymology 68, 342 (1979).
Gene 24, 255 (1983).
Plasmid 6, 67 (1981).
Proc. Natl. Acad. Sci., USA 74, 5463 (1977).
Proc. Natl. Acad. Sci., USA 75, 5765 (1978).
J. Biological Chem. 256, 11283 (1981).
Nucleic Acids Research 11, 3581 (1983).
J. Mol. Biol. 96, 495 (1975).
Nucleic Acids Research 9, 6103 (1981).
Nucleic Acids Research 7, 1513 (1979).
Mol. Gen. Genet. 168, 111 (1979).
Methods in Enzymology 43, 737 (1975).
J. Biol. Chem. 193, 265 (1951).

*Primary Examiner*—Thomas G. Wiseman
*Assistant Examiner*—S. Seidman
*Attorney, Agent, or Firm*—David G. Conlin; Ronald I. Eisenstein

[57] ABSTRACT

A novel recombinant DNA containing the base sequence shown in FIG. 1 or a portion thereof which exhibits promoter activity. The base sequence exhibiting a potent promoter activity is obtained from the chromosomal DNA of strain Bacillus by, for example, cloning with a cloning vector. By growing a transformant of Bacillus transformed with the recombinant DNA carrying a peptide encoding nucleotide, the desired peptide may be produced.

31 Claims, 7 Drawing Figures

5' AATTCCAAGTGTTAATATTCCTTAAAAAACATTTACTTCCATGGAAAATGATGATAGATT

AATTTTTAAGAAAAGAACTGGTAATTCGCGAATTATGAAAAAGCGCTTTTTCTGCA 3'

FIGURE 1

5' AATTCCAAGTGTTAATATTCCTTAAAAAACATTTACTTCCATGGAAAATGATGATAGATT

AATTTTTAAGAAAAAGAACTGGTAATTCGCGAATTATGAAAAAGCGCTTTTTCTGCA 3'

FIGURE 4

```
5'
    GGGGGGGGGGGGGGGGGGATCACTCTCTTTAATCACTACTCACAGTAACC
                S1
TCAACTCCTGCCACA ATG TAC AGG ATG CAA CTC CTG TCT TGC
                                         S20  1
ATT GCA CTA AGT CTT GCA CTT GTC ACA AAC AGT GCA CCT

ACT TCA AGT TCT ACA AAG AAA ACA CAG CTA CAA CTG GAG
                20
CAT TTA CTG CTG GAT TTA CAG ATG ATT TTG AAT GGA ATT
                                              40
AAT AAT TAC AAG AAT CCC AAA CTC ACC AGG ATG CTC ACA

TTT AAG TTT TAC ATG CCC AAG AAG GCC ACA GAA CTG AAA
                    60
CAT CTT CAG TGT CTA GAA GAA GAA CTC AAA CCT CTG GAG
                                                  80
GAA GTG CTA AAT TTA GCT CAA AGC AAA AAC TTT CAC TTA

AGA CCC AGG GAC TTA ATC AGC AAT ATC AAC GTA ATA GTT
                            100
CTG GAA CTA AAG GGA TCT GAA ACA ACA TTC ATG TGT GAA

TAT GCT GAT GAG ACA GCA ACC ATT GTA GAA TTT CTG AAC
120
AGA TGG ATT ACC TTT TGT CAA AGC ATC ATC TCA ACA CTG
133
ACT TGA TAATTAAGTGCTTCCCACTTAAAACATATCAGGCCTTCTATTT
                                                  3'
ATTTAAATATTTAAATTTTACCCCCCCCCCCCCC
```

PROMOTER PLASMID CONTAINING THE PROMOTER AND USE THEREOF IN TRANSFORMING BACILLUS

This invention relates generally to gene manipulation techniques. More particularly, the present invention is concerned with a novel recombinant DNA having promoter activity, a method of producing the same and a transformant of a strain of the genus Bacillus transformed with the recombinant DNA. The present invention is also directed to a process for the production of a peptide using such a transformant.

Gene manipulation techniques have advanced through the use of *Escherichia coil,* and a number of foreign genes have already been expressed in *Escherichia coli.*

*Bacillus subtilis,* which lives in soil, has not been reported as causing animal or plant diseases. Moreover, the use of *Bacillus subtilis* in food processing, such as natto (fermented soybeans) manufacture, has proved the safety of its use. *Bacillus subtilis* is one of the fermentative microorganisms widely used in the industry and the system for controlling the same on an industrial scale has been established. Furthermore, in contrast to *Escherichia coli* which is gram-negative, *Bacillus subtilis* is a gram-positive bacteria which is susceptible to a wide variety of antibiotics, such as $\beta$-lactam antibiotics and macrolide antibiotics which can cause rapid death of viable cells. Because of these favorable characteristics of *Bacillus subtilis,* attention is now being given to the development of foreign gene expression systems using *Bacillus subtilis.*

However, unlike *Escherichia coli,* foreign genes have been expressed in *Bacillus subtilis* only in a few instances due to the unavailability of suitable expression vectors. For example, foreign genes expressed in *Bacillus subtilis* include: expression of the hepatitis B virus C antigen gene and of the foot and mouse disease virus main antigen(VPI) gene [K. Hardy et al., Nature, 293, 481 (1981)], expression of the *Escherichia coli* trp C gene [D. M. Williams et al., Gene, 16, 199 (1981)], expression of the mouse dihydrofolate reductase gene [D. M. Williams et al., Gene, 16, 199 (1981); R. G. Schoner et al., Gene, 22, 47 (1983)], and expression of the human interferon $\beta$ gene [S. Chang et al., Proceedings of the IVth International Symposium on Genetics of Industrial Microorganisms, p. 227 (1982)]. Moreover, the expression yield is in general small and, therefore, the development of a superior expression vector having a potent promoter for *Bacillus subtilis* has been desired. At present, the known *Bacillus subtilis* promoters with the respective base sequences being clarified include the veg promoter, tms promoter, penP promoter, SP01 promoter, 29AI promoter [C. P. Moran Jr. et al., Mol. Gen. Genetics, 186, 339 (1982)], and SP02 promoter [R. G. Schoner et al., Gene, 22, 47 (1983)]. Among them, the SP02 promoter is the only promoter that has actually been utilized in gene expression. Furthermore, the foreign gene products so far expressed are mostly obtained in the form of hybrid or fused proteins.

In accordance with the present invention, there is provided potent gene expression systems for use in *Bacillus subtilis.* More specifically, it has been found that a potent promoter can be obtained from the chromosomal DNA of *Bacillus subtilis.*

In accordance with one aspect of the present invention, there is provided a recombinant DNA including the base sequence given in FIG. 1 or a portion thereof which exhibits promoter activity.

In another aspect, the present invention provides a method of producing a recombinant DNA, comprising inserting a DNA fragment containing the base sequence given in FIG. 1 or a portion thereof which exhibits promoter activity into a vector.

In a further aspect, the present invention provides a transformant of a strain of microorganism belonging to the genus Bacillus transformed with the above recombinant DNA.

In a further aspect, the present invention provides a method of producing a transformant of Bacillus, comprising introducing the above recombinant DNA into a host organism belonging to the genus Bacillus.

In a still further aspect of the present invention, there is provided a process for the production of a peptide, comprising the steps of:

cultivating a transformant obtained by transforming a strain of microorganism belonging to the genus Bacillus with a recombinant DNA containing (a) the base sequence given in FIG. 1 or a portion thereof which exhibits promoter activity and (b) a peptide-encoding nucleotide specific for the peptide located downstream from the nucleotide (a) so that as the transformant grows, there is accumulation of the peptide in the culture; and recovering the peptide from the culture.

The abbreviations as used in the specification, claims and drawings each has the meanings given in Table 1.

Table 1

DNA : Deoxyribonucleic acid
cDNA : Completmentary deoxyribonucleic acid
A : Adenine
T : Thymine
G : Guanine
C : Cytosine
RNA : Ribonucleic acid
mRNA : Messenger ribonucleic acid
dATP : Deoxyadenosine triphosphate
dTTP : Deoxythymidine triphosphate
dGTP : Deoxyguanosine triphosphate
dCTP : Deoxycytidine triphosphate
ATP : Adenosine triphosphate
EDTA : Ethylenediaminetetraacetic acid
SDS : Sodium dodecyl sulfate
Leu : Leucine
Thr : Threonine
Cys : Cysteine
Met : Methionine
Glu : Glutamic acid
Lys : Lysine
His : Histidine
Phe : Phenylalanine
Gln : Glutamine

BRIEF DESCRIPTION OF THE DRAWINGS

FIG. 1 shows the base sequence of a DNA fragment which exhibits promoter activity in *Bacillus subtilis,* the numerals 5' and 3' indicating the 5' end and 3' end, respectively;

FIG. 4 shows the base sequence of the cDNA coding for IL-2 as inserted in the plasmid pILOT135-8, the numerals 5' and 3' indicating the 5' end and 3' end, respectively;

The DNA fragment having the base sequence shown in FIG. 1 of the accompanying drawings can be obtained from chromosomal DNA, derived from a strain of microorganism belonging to the genus Bacillus, by cloning with a promoter cloning vector. The chromosomal DNA may be prepared by known method such as the methods disclosed in Lovett et al (Methods in Enzymology, 68, 342 (1979)). Examples of suitable strains include *Bacillus subtilis* JB-1-168 (IFO-14144), *Bacillus subtilis* 168 and *Bacillus subtilis* MI114. The strain *Bacillus subtilis* 168 is available from The Bacillus Genetic Stock Center under BGSC No. 1A1 [The Bacillus Genetic Stock Center, Catalogue of Strains (Second edition)]. *Bacillus subtilis* MI114 is a known strain described in the literature [Gene, 24, 255 (1983)]and available from The Mitsubishi-Kasei Institute of Life Sciences.

Figure 2:
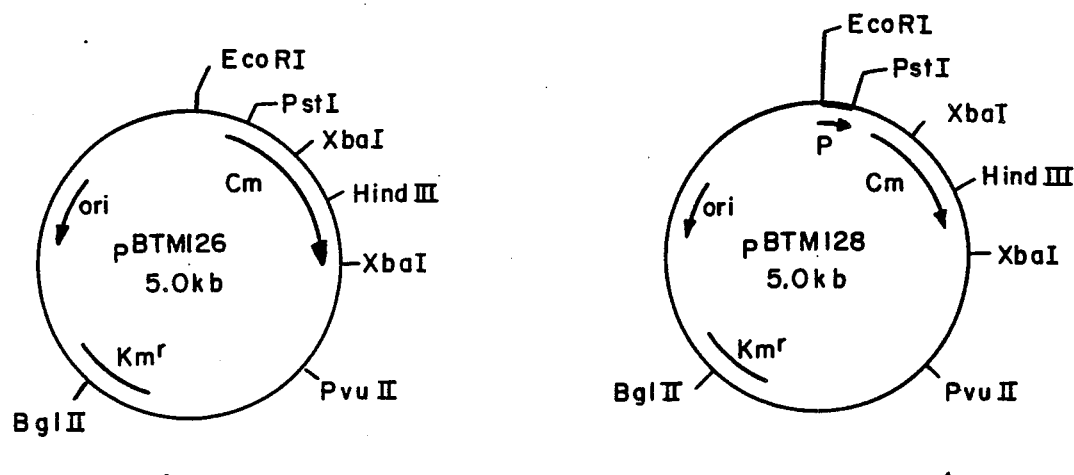
FIG. 2 shows the restriction enzyme maps for the plasmids pBTM126 and pBTM128, respectively, where the symbols Ori, Km$^r$, Cm and $\overline{P}$ indicate the replication startpoint, kanamycin resistance gene, promoter-deficient chloramphenicol resistance gene (chloramphenicol acetyl transferase gene) and promoter, respectively.

The promoter cloning vector is preferably a plasmid into which a chromosomal DNA fragment can be inserted at a restriction enzyme cleavage site and in which, after insertion of such a fragment, the presence of the promoter in the fragment can be confirmed. Such a plasmid is, for example, of a type which contains a promoter portion-deficient gene. The plasmid pBTM126 shown in FIG. 2 is a typical example. The plasmid pBTM126 is identical with the plasmid pPL603 reported by Williams et al. [J. Bacteriol., 146, 1162 (1981)]. The plasmids pBTM126 and pPL603 are constructed from a recombinant plasmid prepared from the Staphylococcus-derived, kanamycin-resistant plasmid pUB110 [Plasmid, 6, 67 (1981)] and the chloramphenicol acetyl transferase (hereinafter sometimes also referred to as "CAT") gene obtained from *Bacillus pumilus* NCIB8600, by eliminating the CAT gene promoter portion. Such plasmids constructed therefrom are lacking in chloramphenicol resistance.

The cloning of the chromosomal DNA fragment having a promoter activity in the cloning vector such as plasmid pBTM126 may be performed by a method which includes the steps of digesting a chromosomal DNA with a restriction enzyme or enzymes to obtain the promoter-containing DNA fragment, and joining the DNA fragment to the cloning vector at its restriction enzyme cleavage sites, for example the EcoRI and PstI sites, using T4 DNA ligase. The resultant product is used for the transformation of *Bacillus subtilis*, followed by isolation of a chloramphenicol-resistant transformant. Promoter activity can be determined by the method of Williams et al. (supra), among others.

The DNA fragment having promoter activity can be isolated from the transformant by known methods, for example by a method including preparing a plasmid from the transformant, digesting the plasmid with a restriction enzyme or enzymes, and subjecting the digestion product to purification such as polyacrylamide gel electrophoresis, agarose gel electrophoresis or the like. The base sequence of the DNA fragment thus obtained can be determined by conventional methods, such as the dideoxynucleotide synthetic chain termination method [Proc. Natl. Acad. Sci. USA, 74, 5463 (1977)].

The cloned product containing the DNA fragment and the promoter cloning vector may be used as such as a recombinant DNA for the construction of an expression vector. Alternatively, the cloned product may be further processed for the substitution of its promoter cloning vector with amother plasmid vector capable of being replicated in *Bacillus subtilis* such as pUB110, pC194, pE194, [The Bacillus Genetic Stock Center, Catalog of Strains (2nd edition)], pBTM119A or pBTM119B [Japanese Published Unexamined Application (Tokkyo Kokai) No. 59-55897 filed Sept. 25, 1982 under an application No. 57-167350].

The DNA fragment shown in FIG. 1 or a portion of the fragment exhibiting promoter activity may also be obtained through chemical synthesis in a conventional manner, for example the phosphotriester method [R. Crea et al., Proc. Natl. Acad Sci. USA, 75, 5765 (1978)].

The DNA fragment according to the present invention has potent promoter activity and is useful as a promoter in constructing an expression vector for use in a strain of genus Bacillus. The DNA fragment is also considered to be useful as a promoter for expression vectors to be used in *Escherichia coli* or actionomycetes.

The desired peptide can be obtained by transforming a strain of the genus Bacillus with a DNA having the above-described DNA fragment or its portion serving as a promoter for the initiation of transcription, a ribosome binding site (SD sequence) located downstream of the promoter and a gene coding for the desired peptide and located downstream of the SD sequence, and cultivating the thus obtained transformant.

The SD sequence may be any of those which are capable of functioning in *Bacillus subtilis*, inclusive of several known ones [J. R. McLaughlin et al, J. Biol. Chem., 256, 11283 (1981); C. P. Moran Jr. et al., Mol. Gen. Genetics, 186, 339 (1982)]. An oligonucleotide containing such an SD sequence can be isolated from a chromosomal DNA or chemically synthesized by the conventional method, for example the phosphotriester method (supra). By inserting the oligonucleotide into a promoter-containing vector downstream from the promoter, the desired plasmid can be constructed. It is advantageous that the oligonucleotide have a restriction enzyme recognition site such as a ClaI site, BamHI site, or SalI site downstream from the SD sequence.

It is preferred that the gene to be expressed have no intervening sequence (intron) and that the base sequence of the gene be known. Such genes include genes isolated from chromosomes, complementary DNAs obtained from mRNAs, chemically synthesized genes, semisynthetic genes. Illustrative of suitable genes are the immune interferon gene, hepatitis B virus (HBV) surface antigen gene, HBV core antigen gene, immunoglobulin E gene, human growth factor gene and interleukin-2 gene. For the production of the desired peptide, it is possible to use either the whole or part of the base sequence of each of the above genes. In constructing expression plasmids by insertion of these genes into expression vectors, an appropriate synthetic oligonucleotide may be joined to the genes, as necessary.

The host, namely a strain of the genus Bacillus, to be transformed with the plasmid obtained in the above manner is not particularly limited to specific strains but include, among others, *Bacillus subtilis* BGCS1A1, BGS1A339 and BGSCaSe40 [The Bacillus Genetic Stock Center, Catalog of Strains (Second edition), 1982]. The transformant is cultivated, for instance, in an L meduim or the like, at 20°–40° C. for 3–48 hours. Thereafter, bacterial cells are collected by known methods and disrupted or lyzed by an appropriate method such as freezing and thawing, addition of lysozyme, sonication, addition of a surfactant, or a combination of these. The peptide produced can then be extracted. The peptide extracted can be purified by the conventional peptide purification method to give the desired peptide.

The present invention also provides an effective method of extracting human immune interferon. The method comprises cultivating a strain of microorganism belonging to the genus Bacillus which carries the human immune interferon gene, harvesting bacterial cells, lyzing or disrupting the cells by a combination of two or more of the freezing and thawing method, lysozyme addition method and sonication method, and extracting human immune interferon.

The freezing and thawing method is preferably carried out by freezing the cells at $-20°$ C. to $-160°$ C. followed by thawing at about $+4°$ C. over a thawing period of about 10 seconds to 3 minutes.

The lysozyme to be used in the lysozyme addition method may be of any kind and is added, in cases where the cell concentration is about $1\times10^4$ to $1\times10^{10}$ cells/ml, in an amount to produce a final concentration of about 50–5000 µg/ml, preferably about 500–1000 µg/ml. The treatment is preferably conducted at about $+15°$ to $+40°$ C., preferably about $+28°$ C. to $+37°$ C. The treatment time depends on the kind and amount of lysozyme and on the treatment temperature but generally 5 minutes to 30 minutes is preferred.

The sonication method is preferably carried out at a wavelength of about 10 KHz to 30 KHz for about 5–60 seconds, preferably 5–20 seconds to thereby cause cell disruption.

Cell disruption by a combination of two of the above three methods allows easy extraction of human immune interferon. The combination of the three methods is more preferred.

A variety of surfactants and/or a protease inhibitor may be added as necessary.

The following reference examples, working examples and the accompanying drawings will further illustrate the invention. It is to be noted, however, that such examples are by no means limitative of the present invention.

REFERENCE EXAMPLE 1

Construction of promoter cloning vector pBTM126

A plasmid pBTM126 was constructed by the method of Williams et al.(supra) in the following manner. DNA was prepared from *Bacillus pumilus* NCIB8600 (IFO-12089) provided by The Institute for Fermentation, Osaka, and the DNA (6.5 µg) was cleaved by treatment with 40 units of the restriction enzyme EcoRI at 37° C. for 1 hour, followed by heating at 68° C. for 15 minutes and the subsequent precipitation with ethanol. Separately, the plasmid PUB110 (2.0 µg) was cleaved by treatment with 20 units of the restriction enzyme EcoRI at 37° C. for 1 hour, followed by heating at 68° C. for 15 minutes and precipitation with ethanol. Both the precipitates were respectively dissolved in water and the solutions were combined, 60 nmoles of ATP, 10 units of T4 DNA ligase (Takara Shuzo, Japan) and ligase buffer were added thereto, and the mixture (100 µl) was maintained at 11° C. for 30 hours. Ethanol precipitation was conducted and the precipitate dissolved in TE buffer (50 µl), and 25 µl of the solution used for transformation of *Bacillus subtilis* MI114. A plasmid was prepared from a chloramphenicol resistant transformant and named pBTM124. Then, the plasmid pBTM124 (2.5 µg) was cleaved by treatment with 14 units of the restriction enzyme PstI at 37° C. for 1 hour, followed by heat treatment at 68° for 15 minutes and ethanol precipitation. The precipitate was dissolved in water, to which 66 nmoles of ATP, 10 units of T4 DNA ligase (Takara Shuzo, Japan) and ligase buffer were added, and the mixture (100 µl) was maintained at 11° C. for 24 hours, followed by precipitation with ethanol. The precipitate was dissolved in TE buffer and used for transformation of *Bacillus subtilis* MI114. A plasmid was prepared from one of the resulting kanamycin resistant transformants and named pBTM125. This plasmid was lacking in the promoter region (PstI fragment) of CAT gene of the plasmid pBTM124. The plasmid pBTM125 (2.5 µg) was cleaved by treatment with 18 units of the restriction enzyme BamHI and 15 units of the restriction enzyme BglII at 37° C. for 1 hour, followed by heating at 68° C. for 15 minutes and precipitation with ethanol. The precipitate was dissolved in water and maintained in a reaction medium (100 µl) containing 66 nmoles of ATP, 13 units of T4 DNA ligase (Takara Shuzo, Japan) and ligase buffer at 11° C. for 28 hours, and used for transformation of *Bacillus subtilis* MI114. A plasmid was prepared from one of the resulting kanamycin resistant transformants and named pBTM126.

REFERENCE EXAMPLE 2

Construction of plasmid pHITtrp2101

The immune interferon (IFN-γ) cDNA-containing plasmid pHIT3709 and an expression vector ptrp601 were constructed by the procedure described in Japanese patent publication No.189197/1983 basically corresponding to EP-0089676.

First, the plasmid pHIT3709 was cleaved with the restriction enzyme PstI, and the thus-obtained PstI fragment containing the structural gene for IFN-γ was partially cleaved with the restriction enzyme BstNI to give a BstNI-PstI fragment as a product of cleavage at the BstNI site in the IFN-γ structural gene. The cohesive end at the BstNI cleavage site was filled in with DNA polymerase I large fragment. Then, an oligonucleotide adapter chemically synthesized by the phosphotriester method and containing the translation start codon ATG
CGATAATGTGTTACTGCC
TATTACACAATGACGG was joined to the above fragment using T4 DNA ligase.

Separately, an IFN-γ expression plasmid pHITtrp1101 was constructed by inserting the IFN-γ gene, with the above adapter joined thereto, into a fragment obtained by cleavage of ptrp771 [Y. Fujisawa et al., Nucleic Acids Research, 11, 3581 (1983)] with the restriction enzyme PstI and the restriction enzyme ClaI, downstream from the tryptophan promoter, with T4 DNA ligase used for effecting the joining.

Then, ptrp601 was treated with the restriction enzyme ClaI and the restriction enzyme HpaII. The thus-obtained 0.33 Kb ClaI-HpaII fragment containing the trp promoter was cleaved with ClaI and joined to alkaline phosphatasetreated pHITtrp1101 using T4 DNA ligase, to give pHITtrp2101 with two trp promoters inserted therein in series.

REFERENCE EXAMPLE 3

(i) Isolation of mRNA coding for human IL-2

Human peripheral blood lymphocytes were cultured in RPMI 1640 medium (containing 10% of fetal calf serum) containing 12-0-tetradecanoylphorbol-13-acetate (TPA) (15 ng/ml) and concanavalin A (40 µg/ml) at 37° C. to thereby induce IL-2 production. After 24 hours of incubation, $1 \times 10^{10}$ of the human lymphocytes thus induced were disrupted and denatured in a solution containing 5 M guanidine thiocyanate, 5% mercaptoethanol, 50 mM Tris-HCl (pH 7.6) and 10 mM EDTA using a Teflon homogenizer, followed by addition of sodium N-lauroylsarcosinate to a concentration of 4%. The homogenized mixture was layered on 6 ml of 5.7 M cesium chloride solution (5.7 M cesium chloride, 0.1 M EDTA), followed by centrifugation at 24000 rpm and 15° C. for 48 hours using a Beckman SW 28 rotor. The RNA precipitate thus obtained was dissolved in 0.25% sodium N-lauroylsarcosinate solution and then precipitated with ethanol. The thus-obtained RNA (10 mg) was applied to an oligo(dT)cellulose column in a high concentration salt solution (0.5 M NaCl, 10 mM Tris-HCl (pH 7.6), 1 mM EDTA, 0.3% SDS) for adsorption and then eluted with a low concentration salt solution (10 mM Tris-HCl (pH 7.6), 1 mM EDTA, 0.3% SDS) containing poly(A), whereby 300 µg of poly(A)-containing mRNA.

This mRNA was further subjected to ethanol precipitation and then dissolved in 0.2 ml of a solution (10 mM Tris-HCl (pH 7.6), 2 mM EDTA, 0.3% SDS). After treatment at 65° C. for 2 minutes, centrifugation (Beckman SW 28 rotor; 20° C., 25000 rpm, 21 hours) was performed on a 10–35% sucrose density gradient, whereby 22 fractions were obtained. For each fraction, part of RNA was injected into the *Xenopus laevis* oocyte and the IL-2 activity in the protein synthesized was measured. For fractions 11-15 (sedimentation coefficient 8S-15S), IL-2 activity was detected. The IL-2 mRNA in these fractions weighed about 25 µg.

(ii) Synthesis of single-stranded DNA

Using the mRNA obtained in the above and reverse transcriptase, incubation was performed in 100 µl of a reaction medium (5 µg of mRNA, 50 µg of oligo(dT), 100 units of reverse transcriptpase, 1 mM dATP, 1 mM dCTP, 1 mM dGTP, 1 mM dTTP, 8 mM MgCl₂, 50 mM KCl, 10 mM dithiothreitol, 50 mM Tris-HCl (pH 8.3)) at 42° C. for 1 hour. Deproteinization was effected with phenol, followed by treatment with 0.1 N NaOH at 70° C. for 20 minutes for decomposition and removal of RNA.

(iii) Synthesis of double-stranded DNA

Double-stranded DNA was synthesized by subjecting the single-stranded complementary DNA synthesized hereinabove to reaction in 50 µl of a reaction medium [same reaction medium as above except for the absence of mRNA and oligo(dT)] at 42° C. for 2 hours.

(iv) Addition of dC tail

This double-stranded DNA was allowed to undergo the action of S1 nuclease in 50 µl of a reaction medium (double stranded DNA, 0.1 M sodium acetate pH 4.5, 0.25 M NaCl, 1.5 mM ZnSO₄, 60 units of S1 nuclease) at room temperature for 30 minutes, followed by deproteinization with phenol and precipitation with ethanol. The precipitated DNA was allowed to undergo the action of terminal transferase in 50 µl of a reaction medium (double-stranded DNA, 0.14 M potassium cacodylate, 0.3 M Tris (base) (pH 7.6), 2 mM dithiothreitol, 1 mM CoCl₂, 0.15 mM dCTP, 30 units of terminal transferase) at 37° for 3 minutes to thereby extend the 3' end of the double-stranded DNA by a chain of 15 deoxycytidines. The above series of reactions gave about 300 ng of a deoxycytidine chain-containing double-stranded DNA.

(v) Cleavage of *Escherichia coli* plasmid and addition of dG tail

Separately, 10 µg of the *Escherichia coli* plasmid pBR322 DNA was cleaved with the restriction enzyme PstI in 50 µl of a reaction medium (10 µg of DNA, 50 mM NaCl, 6 mM Tris-HCl (pH 7.4), 6 mM MgCl₂, 6 mM 2-mercaptoethanol, 100 µg/ml bovine serum albumin, 20 units of PstI) at 37° C. for 3 hours to thereby cleave the only one PstI recognition site occurring in the pBR322 DNA. Following deproteinization with phenol, the DNA was allowed to undergo the action of terminal transferase in 50 µl of a reaction medium (10 µg of DNA, 0.14 M potassium cacodylate, 0.3 M Tris base (pH 7.6), 2 mM dithiothreitol, 1 mM CoCl₂, 0.15 mM dGTP, 30 units of terminal transferase) at 37° C. for 3 minutes to thereby extend the 3' end of the above plasmid pBR322 by about 17 deoxyguanines.

(vi) Annealing of cDNA and transformation of *Escherichia coli*

For annealing, 0.1 µg of the synthetic double-stranded DNA thus obtained and 0.5 µg of the above-mentioned plasmid pBR322 were heated in a solution comprising 0.1 M NaCl, 50 mM Tris-HCl (pH 7.6) and 1 mM EDTA at 65° C. for 2 minutes and then at 45° C. for 2 hours, and cooled gradually. Transformation of *Escherichia Coli* MM294 was conducted in accordance with the method of Enea et al. [J. Mol. Biol., 96, 495 (1975)].

(vii) Isolation of cDNA-containing plasmid

In this way, about 20 000 tetracycline-resistant were isolated. DNA of each of them was immobilized on a nitrocellulose filter. Then, based on the amino acid sequence of IL-2 as reported by Taniguchi et al. [Nature, 302, 305 (1983)], two base sequences (5' AAA CAT CTT CAG TGT³' and 5' ACA TTC ATG TGT GAA 3') corresponding to the amino acids Nos. 74–78 (Lys[74]-His-Leu-Gln-Cys) and the amino acids Nos. 122–126 (Thr[122]-Phe-Met-Cys-Glu), respectively, were chemically synthesized by the phosphotriester method [R. Crea et al., Proc. Natl. Acad. Sci. USA, 75, 5765 (1978)].

Figure 3:
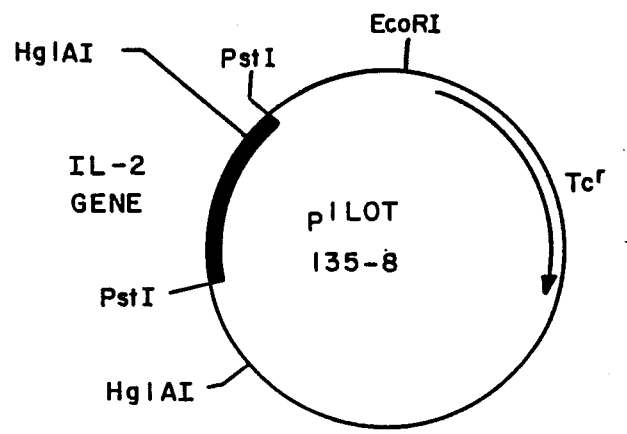
FIG. 3 shows the plasmid pILOT135-8, Tc$^r$ indicating the tetracycline resistance gene.

Using T4 polynucleotide kinase, these oligonucleotides were labeled with $^{32}$p at the 5' end by treating in 50 μl of a reaction medium (0.20 μg of oligonucleotide, 50 mM Tris-HCl (pH 8.0), 10 mM MgCl$_2$, 10 mM mercaptoethanol, 50 μCiγ-$^{32}$p-ATP, 3 units of T4 polynucleotide kinase) at 37° C. for 1 hour. These labeled oligonucleotides were used as probes and associated with the above-mentioned DNA immobilized on the nitrocellulose filter by the method of Lawn et al. [Nucleic Acids Res., 9, 6103 (1981)]. Autoradiography indicated four colonies responsive to the above two oligonucleotide probes. Plasmid DNA was isolated from the bactrial cells of each of these colonies by Birnboim-Doly's alkali method [H. C. Birnboim & J. Doly, Nucleic Acids Res., 7, 1513 (1979)]. The insert in the plasmid DNA was excised using the restriction enzyme PstI. From among the plasmids isolated, the one containing the longest insert was chosen and named "pILOT135-8" (FIG. 3).

The primary structure (base sequence) of the cDNA sequence inserted in the plasmid pILOT135-8 was then determined by the dideoxynucleotide synthesis chain termination method and by the Maxam-Gilbert method. Said primary structure is shown in FIG. 4. The peptide defined by this base sequence comprises of 153 amino acids, the synthesis of which starts from the synthesis initiation signal therefor (ATG with Nos. 64–66). The first 20 amino acids from the N terminal presumably constitute a signal peptide. The above primary structure indicated that this plasmid had the whole base sequence coding for the human IL-2 protein. This fact means that the gene inserted in the plasmid can be inserted into another expression plasmid so that any polypeptide species of the IL-2 protein can optionally be produced.

(viii) Cleavage of the plasmid pILOT135-8 using the restriction enzyme HgiAI gave a 1294 bp DNA fragment containing the IL-2 gene. After treatment with T4 DNA polymerase, this DNA fragment was ligated with the ClaI linker CGATA ATG GCA containing the codon GCA for alanine and the codon ATG for methionine, followed by treatment with ClaI and insertion into ptrp771 (Y. Fujisawa et al., vide supra) at the ClaI site thereof. The thus-obtained plasmid was named pTF5.

EXAMPLE 1

Cloning of promoter

The promoter cloning vector pBTM126 (2.1 μg) obtained in Reference Example 1 was cleaved with the restriction enzyme PstI (8 units) at 37° C. for 1 hour and further with the restriction enzyme EcoRI (5 units) at 37° C. for 1 hour. The cleavage reaction was terminated by heating at 68° C. for 15 minutes. Then, ethanol was added to cause precipitation. Separately, the chromosome (6.2 μg) of *Bacillus subtilis* JB-1-168 (IFO-14144) was cleaved with PstI (24 units) and EcoRI (15 units) respectively at 37° C. for 1 hour, followed by heating at 68° for 15 minutes and precipitation with ethanol. Both the precipitates, after being dissolved in water, were mixed and the mixture was allowed to react in the presence of ATP (66 nmoles) and T4 DNA ligase (10 units; Takara Shuzo,Japan) at 11° C. for 24 hours, followed by precipitation with ethanol. The precipitate was dissolved in TE buffer (10 mM Tris-HCl buffer (pH 8.0), 1 mM EDTA) and used for transformation of B. subtilis MI114 by the protoplast method [S. Chang and S. N. Cohen, Mol. Gen. Genet., 168, 111 (1979)]. Selective culture on DM3 agar plates [Mol. Gen. Genet., 168, 111 (1979)]containing 12.5 μg/ml of chloramphenicol gave 956 transformant colonies. The subsequent replica plating using brain-heart infusion (Difco, USA) agar plates containing 200 μg/ml of chloramphenicol allowed 20 colonies to grow. These transformants were found to carry a plasmid with the DNA fragment having potent promoter activity.

EXAMPLE 2

Measurement of promoter activity

One of the 20 transformants obtained in Example 1, namely *Bacillus subtilis* T48 [Bacillus subtilis MI114 containing the plasmid pBTM128(cf. FIG. 2)]was used for the measurement of its promoter activity according to the method of Williams et al(supra). The strains of *Bacillus subtilis* MI114 carrying the plasmid pBTM124 (containing the promoter-containing CAT gene) as obtained in Reference Example 1 and pBTM126 (containing the promoter-deficient CAT gene), respectively, were used as controls.

First, each strain was cultured in a 200-ml Erlenmeyer flask containing 40 ml of L medium, with or without 5 μg/ml of chloramphenicol, with shaking at 30° C. for 16 hours. Then, 10 ml of each culture obtained was centrifuged and the bacterial cells collected were washed with 20 mM Tris-HCl buffer (pH 7.8). The cells were suspended in 1 ml of the same buffer containing 0.5 mg/ml of lysozyme, incubated at 37° C. for 25 minutes and then treated in a sonicator at 2A for 10 seconds, and the supernatant was submitted, as an enzyme solution, to activity measurement. CAT activity measurement was performed by the colorimetric method using 5,5'-dithio-bis(2-nitrobenzoic acid) [Methods in Enzymology, 43, 737 (1975)]. Protein determination was carried out by the method of Lowry et al. [J. Biol. Chem., 193, 265 (1951)]. The results thus obtained are shown in Table 2.

TABLE 2

| Transformant | Specific activity (mol/min/mg protein) | |
|---|---|---|
| | +Cm | −Cm |
| B. subtilis MI114/pBTM124 | 2.2 | 0.17 |
| B. subtilis MI114/pBTM126 | 0 | 0 |
| B. subtilis MI114/pBTM128 (B. subtilis T48) | 15 | 0.84 |

In the above table, "+Cm" indicates L medium containing 5 μg/ml of chloramphenicol and "−Cm" chloramphenicol-free L medium. The above evidenced that the DNA fragment cloned in pBTM128 had potent promoter activity.

EXAMPLE 3

Preparation of plasmid pBTM128

*Bacillus subtilis* T48 was cultivated with shaking in L medium (500 ml) containing 1% of tryptone (Difco, USA), 0.5% of yeast extract (Difco, USA) and 0.5% of sodium chloride (pH 7.2) at 28° C. for 16 hours. Cells were harvested by centrifugation of the culture thus obtained (500 ml). Thereto were added 60 ml of TES buffer (30 mM Tris-HCl (pH 8.0)- 50 mM NaCl - 5 mM EDTA) containing 25% of sucrose, 12 ml of 0.25 M EDTA (pH 8.0), 16 ml of 5 mg/ml lysozyme solution and 0.8 ml of 5 mg/ml ribonuclease A solution, followed by incubation at 37° C. for 30 minutes. Then, 8 ml of 10% sodium lauryl sulfate was added, followed by further incubation at 37° C. for 15 minutes. Then, 20 ml of 5 M sodium chloride was added and the mixture was allowed to stand at 0° C. for 3 hours and then centrifuged. Two volumes of cold ethanol was added to the supernatant. After allowing at −20° C. overnight, the mixture was centrifuged. The precipitate obtained was dissolved in 8.6 ml of TES buffer containing 0.4% of sodium N-lauryl sarcosinate (Sarkosyl) and, following addition of 9 g of cesium chloride and 0.25 ml of 30 mg/ml ethidium bromide solution, centrifuged at 38,000 rpm and 20° C. for 48 hours using a Beckman ultracentrifuge (rotor 50 Ti). The plasmid band detected by ultraviolet irradiation was collected, a cesium chloride-ethidium bromide solution (specific gravity =1.6) added thereto, and the mixture again centrifuged at 55,000 rpm and 20° C. for 6 hours using a Beckman ultracentrifuge (Vti 65 rotor). The plasmid band was collected, from which ethidium bromide was removed by extraction with n-butanol, and dialyzed against TE buffer to give the plasmid pBTM128 (cf. FIG. 2). The absorbance at 260 nm showed that the yield of the plasmid was about 330 μg.

EXAMPLE 4

Isolation of promoter DNA fragment and properties thereof

The plasmid pBTM128 (221 μg) obtained in Example 3 was digested with PstI (208 units) and EcoRI (220 units), respectively at 37° C. for 1 hour, followed by 10% polyacrylamide gel electrophoresis. The gel was stained by immersion in an ethidium bromide solution. The promoter DNA fragment detected under an ultraviolet lamp was recovered. After the DNA fragment was extracted from the gel by electric elution, the DNA fragment was extracted with phenol, and then with ether and precipitated with ethanol. The precipitate was dissolved in TE buffer, and 3.55 μg of the promoter DNA fragment was isolated.

The size of the promoter DNA fragment obtained was measured by 4% polyacrylamide gel electrophoresis and calculated to be about 120 bp using a HaeIII digestion product from the plasmid pBR322 as a standard. The base sequence of said fragment was determined by the dideoxynucleotide synthetic chain termination method (supra) to be the one given in FIG. 1. This fragment consists of 117 bp and has an EcoRI cleavage site at the 5' end and a PstI cleavage site at the 3' end. In the fragment, base sequences are observed which are presumably the −10 and −35 regions.

EXAMPLE 5

Construction of expression vector pBTM134

Figure 5:
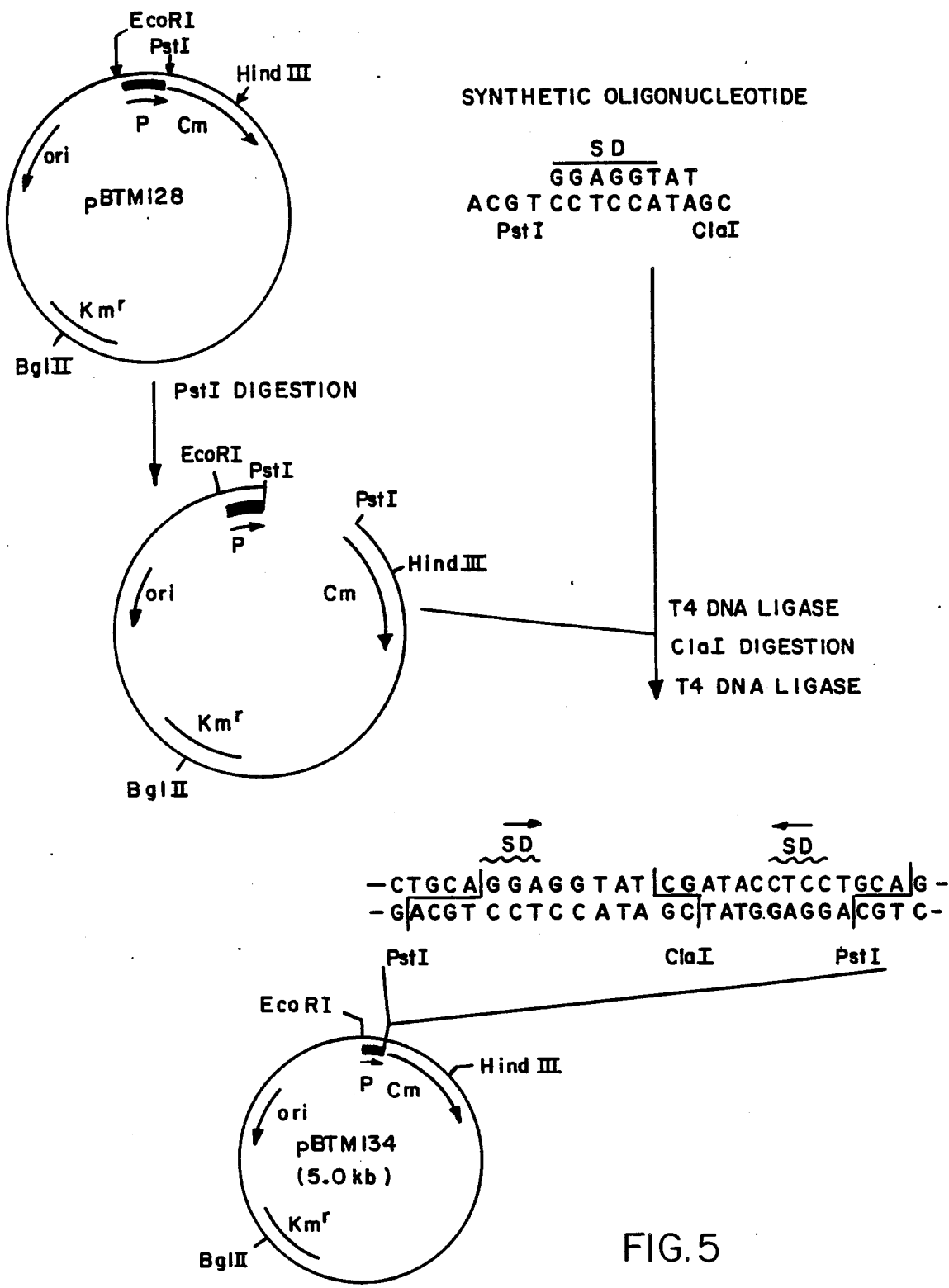
FIG. 5 shows a scheme for constructing the plasmid pBTM134, the symbols Ori, Km$^r$, Cm, $\overline{P}$ and $\overline{SD}$ indicating the replication startpoint, kanamycin resistance gene, promoter-deficient chloramphenicol resistance gene (chloramphenicol acetyl transferase), promoter and ribosome binding site, respectively.

The plasmid pBTM128(7.7 μg) obtained in Example 3 was digested with the restriction enzyme PstI (51 units) at 37° C. for 1 hour and then treated with 0.75 unit of *Escherichia coli* alkaline phosphatase at 65° C. for 30 minutes. The reaction product was extracted with phenol, extracted with ether and precipitated with ethanol. The thus-collected precipitate was dissolved in a small amount of water. Thereto were added an 8-base synthetic nucleotide GGAGGTAT (200 ng) phosphorylated at the 5' end, a 14-base synthetic nucleotide CGATACCTCCTGCA (350 ng) phosphorylated at the 5' end, 100 nanomoles of ATP, 28 units of T4 DNA ligase (Takara Shuzo, Japan) and a ligase buffer, and the mixture (100 μl) was maintained at 11° C. for 20 hours, followed by precipitation with ethanol. The precipitate was dissolved in a small amount of water and digested with 25 units of ClaI at 37° C. for 1 hour. Small-sized oligonucleotides were removed by means of a Sepharose 4B column, and the desired product was collected by precipitation with ethanol. The precipitate was dissolved in water. Thereto were added 100 nmoles of ATP, 28 units of T4 DNA ligase (Takara Shuzo, Japan) and a ligase buffer, and the resulting mixture (100 μl) was maintained at 11° C. for 20 hours to thereby ligate each other at the ClaI site, and 50 μl of the reaction mixture used for transformation of *Bacillus subtilis* MI114 by the protoplast method (vide supra). A plasmid was isolated from a kanamycin- and chloramphenicol-resistant transformant and named pBTM134 (cf. FIG. 5).

EXAMPLE 6

Expression of human immune interferon gene

To 5 μg of the 1.03 Kb ClaI-PstI fragment containing the human immune interferon gene as obtained from the plasmid pHITtrp2101 obtained in Reference Example 2, there were added an 8-base synthetic oligonucleotide GATCGATC (300 ng) phosphorylated at the 5' end, a 12-base synthetic oligonucleotide GATCGATCTGCA (450 ng) phosphorylated at the 5' end, 100 nanomoles of ATP, 2000 units of T4 DNA ligase (New England BioLabs, USA) and a ligase buffer and the mixture (100 μl) was kept at 11° C. for 24 hours, followed by precipitation with ethanol. The precipitate was dissolved in water and digested with 25 units of the restriction enzyme ClaI at 37° C. for 1 hour. Small-sized oligonucleotides were removed by means of a Sepharose 4B column (1.5 ml) and the precipitation with ethanol gave a DNA fragment comprising the human immune interferon gene with ClaI sites at both ends thereof.

Figure 6:
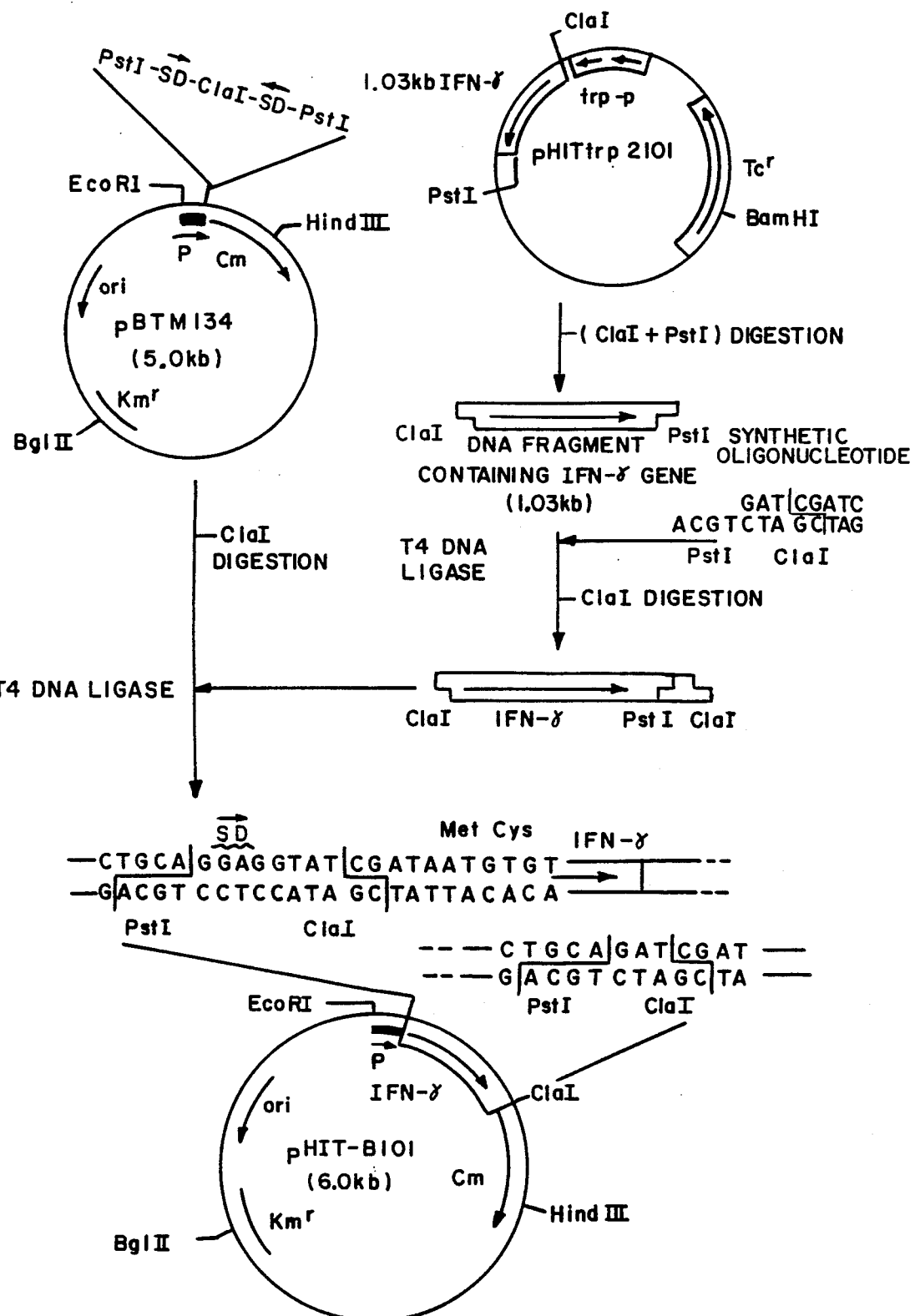
FIG. 6 shows a scheme for constructing the plasmid pHIT-B101, the symbols Ori, Km$^r$, Cm, $\overline{P}$, $\overline{SD}$, Tc$^r$, trp-P and IFN-γ indicating the replication startpoint, kanamycin resistance gene, promoter-deficient chloramphenicol resistance gene (chloramphenicol acetyl transferase gene), promoter, ribosome binding site, tetracycline resistance gene, trp promoter and human immune interferon gene, respectively.
Figure 7:
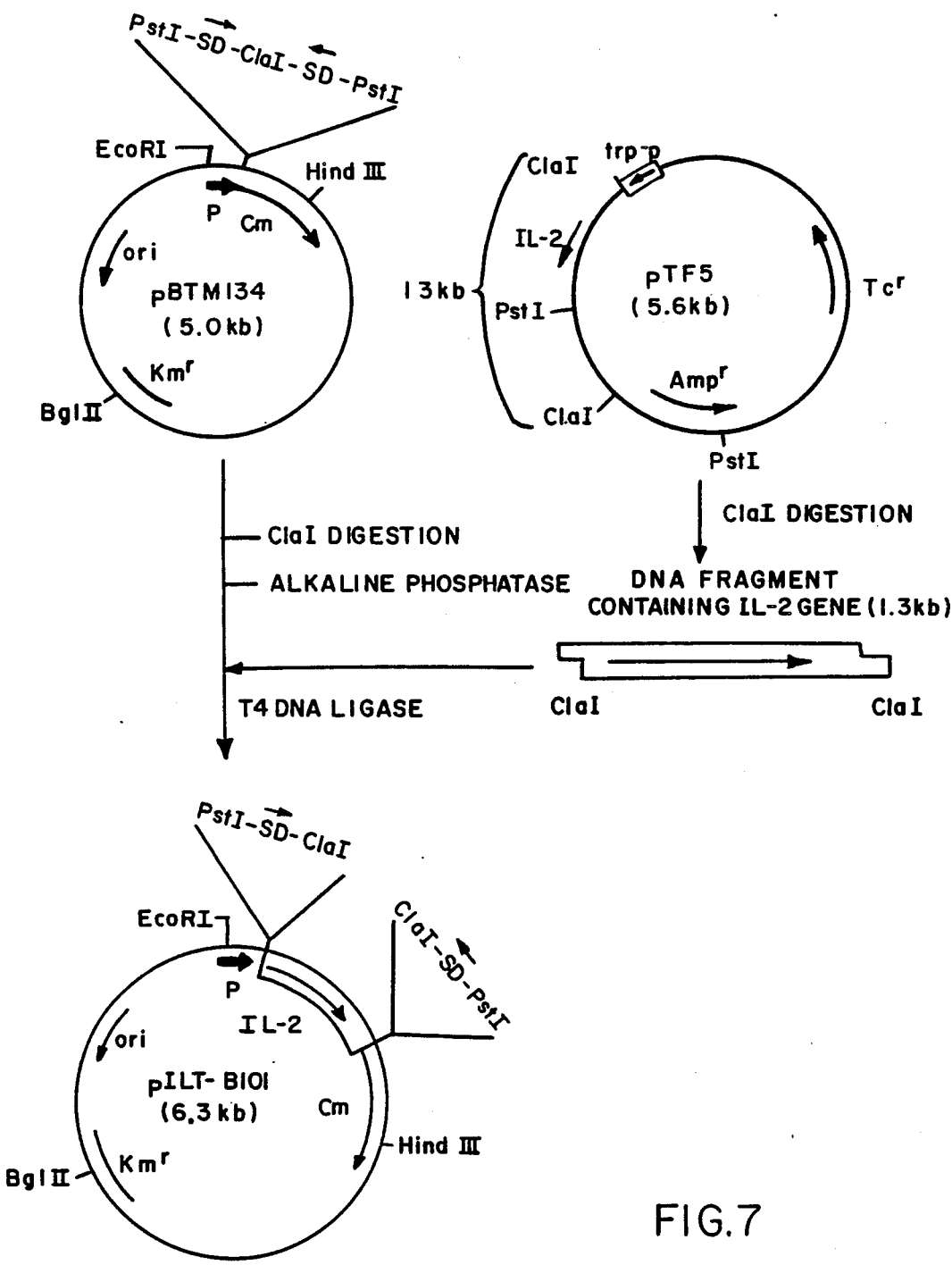
FIG. 7 shows a scheme for constructing the plasmid pILT-B101, the symbols Ori, Km$^r$, Cm, $\overline{P}$, $\overline{SD}$, Tc$^r$, Amp$^r$, trp-P and IL-2 indicating the replication startpoint, kanamycin resistance gene, promoter-deficient chloramphenicol resistance gene, promoter, ribosome binding site, tetracycline resistance gene, ampicillin resistance gene, trp promoter and interleukin-2 gene, respectively.

Separately, 1.1 μg of the expression vector pBTM134 obtained in Example 5 was cleaved with 10 units of ClaI at 37° C. for 1 hour, further treated with 0.1 unit of *Escherichia coli* alkaline phosphatase at 65° C. for 30 minutes and extracted with phenol. The extract was then extracted with ether, followed by precipitation with ethanol. This precipitate and the above precipitate were each dissolved in a small amount of water and the solutions were mixed. To the mixture, there were further added 100 nmoles of ATP, 1200 units of T4 DNA ligase (New England BioLabs) and a ligase buffer and the resulting mixture (100μl) was kept at 11° C. for 24 hours and then used for transformation of *Bacillus subtilis* MI114 by the protoplast method. Plasmids were isolated from kanamycin-resistant transformants, and the one with the human immune interferon gene-containing DNA fragment inserted in pBTM134 at the ClaI site in the sense direction was named pHIT-B101 (cf. FIG. 6) and the other with said fragment inserted therein in the anti-sense direction pHIT-B102.

The strains of *Bacillus subtilis* MI114 carrying the plasmid pBTM134, pHIT-B101 and pHIT-B102 respectively were inoculated from an agar medium into a 200-ml Erlenmeyer flask containing 40 ml of L medium (containing 5 μg/ml of kanamycin) and culture was inoculated at 37° C. for 5 hours with shaking, when the $OD_{600}$ reached 1.2. The culture obtained was centrifuged, the cells collected were washed twice with 30 mM Tris-HCl buffer (pH 8.0)- 50 mM NaCl - 5 mM EDTA and frozen in dry ice-ethanol (−70° C.), and the frozen cells were suspended in 2 ml of 50 mM Tris-HCl buffer (pH 8.0)- 10% sucrose - 100 mM NaCl - 10 mM EDTA 20 mM spermidine - 1 mg/ml albumin. Following addition of 40 μl of 20 mg/ml lysozyme solution, the mixture was kept at 37° C. for 20 minutes and then sonicated at 19.5 KHz for 10 seconds, followed by centrifugation at 15000 rpm for 15 minutes. The supernatant was submitted, as a sample, to human immune interferon assay.

The human immune interferon obtained above was assayed for antiviral activity by the test for its ability to inhibit the cytopathic effect of vesicular stomatitis virus (VSV) on human amnion-derived WISH cells. With the Bacillus subtilis MI114 strains carrying the plasmids pBTM134 and pHIT-B102, no human immune interferon activity was observed, whereas, with the Bacillus subtilis MI114 strain carrying the plasmid pHIT-B101 [Bacillus subtilis MI114/pHIT-B101], a human immune interferon activity of 1238 units/ml (extract) was found.

EXAMPLE 7

Expression of IL-2 gene

The plasmid pBTM134 (1 μg) was digested with the restriction enzyme ClaI (10 units) at 37° C. for 1 hour and then further treated with 0.1 unit of Escherichia coli alkaline phosphatase at 65° C. for 30 minutes. The reaction mixture was extracted with phenol and then with ether. Addition of ethanol gave a precipitate of DNA. Separately, from the plasmid pTF5 having the IL-2 gene as obtained in Reference Example 3, a 1.3 Kb ClaI fragment containing the IL-2 gene was isolated. The ClaI digestion product (0.5 μg) from the plasmid pBTM134 as obtained above and the 1.3 Kb ClaI DNA fragment (0.6 μg) were mixed, 100 nmoles of ATP, 2000 units of T4 DNA ligase (New England BioLabs) and a ligase buffer were added, and the resultant mixture (100 μl) was kept at 11° C. for 24 hours to thereby join the 1.3 Kb ClaI DNA fragment to pBTM134. The reaction product was used for transformation of Bacillus subtilis MI114. Plasmid preparation from the kanamycin-resistant strains obtained gave two plasmids with the IL-2 gene containing 1.3 Kb DNA fragment inserted in the plasmid pBTM134 at the ClaI site thereof in the right and reverse directions, respectively. The plasmids were named pILT-B101 and pILT-B102, respectively. The directionality of the DNA fragment was determined by using the restriction enzymes EcoRI and XbaI. The strain of Bacillus subtilis MI114 carrying the plasmid pILT-B101 [Bacillus subtilis MI114/pILT-B101]has been deposited with the Institute for Fermentation, Osaka, under No. IFO-14305, and deposited at Fermentation Research Institute, Agency of Industrial Science and Technology, Ministry of International Trade and Industry, Japan(FRI) under the Budapest Treaty under the accession number of FERM BP-610.

The strains of Bacillus subtilis MI114 carrying the plasmids pBTM134, pILT-B101 and pILT-B102 respectively were cultured in 40 ml of L medium (containing 5 μg/ml of kanamycin) in a 200-ml Erlenmeyer flask with shaking at 37° C. for 4 hours. The $OD_{600}$ reached 1.1–1.5. The culture thus obtained was centrifuged, the cells thus collected were washed 3 times with 1 M KCl and first frozen in dry ice-ethanol (−70° C.). The frozen cells were suspended in 2 ml of 30 mM Tris-HCl (pH 8.0) - 50 mM NaCl - 5 mM EDTA - 1 mg/ml albumin. Following addition of 50 ul of 20 mg/ml lysozyme solution, the mixture was kept at 37° C. for 15 minutes and then treated in a sonicator at 19.5 KHz for 10 seconds. The sonication product was centrifuged at 10000 rpm for 10 minutes and the supernatant was submitted to IL-2 assay.

The assay for IL-2 was performed by measuring the promotion of growth of IL-2-dependent mouse NKC3 cells in terms of $^3$H-thymidine uptake. Table 3 shows the IL-2 activity for each plasmid-carrying strain.

TABLE 3

| Transformant | Directionality of IL-2 gene | IL-2 activity (units/liter of culture) |
|---|---|---|
| B. subtilis MI114/pBTM134 | — | <5 |
| B. subtilis MI114/pILT-B101 | Sense | 350 |
| B. subtilis MI114/pILT-B102 | Anti-Sense | <5 |

The following references, which are referred to for their disclosures at various points in this application, are incorporated herein by reference.

Nature., 293, 481 (1981)
Gene., 16, 199 (1981)
Gene., 22, 47 (1983)
Proceedings of the IVth International Symposium on Genetics of Industrial Microorganisms.,p.227(1982)
Mol. Gen. Genetics., 186, 339 (1982)
Methods in Enzymology., 68, 342 (1979)
Gene., 24, 255 (1983)
J. Bacteriol., 146, 1162 (1981)
Plasmid., 6, 67 (1981)
Proc. Natl. Acad. Sci. USA., 74, 5463(1977)
Japanese Published Unexamined Application (Tokkyo Kokai) No. 59-55897 (filed on Sept. 25, 1984)
Proc. Natl. Acad. Sci. USA., 75, 5765 (1978)
J. Biol. Chem., 256, 11283 (1981)
Nucleic Acids Research., 11, 3581 (1983)
J. Mol. Biol., 96, 495 (1975)
Nucleic Acids Research., 9, 6103 (1981)
Nucleic Acids Research., 7, 1513 (1979)
Mol. Gen. Genet., 168, 111 (1979)
Methods in Enzymology., 43, 737 (1975)
J. Biol. Chem., 193, 265 (1951)

We claim:

1. A recombinant DNA segment including the base sequence depicted in FIG. 1 or a portion thereof, which exhibits promoter activity and a gene which is heterologous to Bacillus.

2. A recombinant DNA segment as claimed in claim 1, which includes the base sequence given in FIG. 1.

3. A recombinant DNA segment as claimed in claim 1, which further includes a plasmid joined to said base sequence or said portion.

4. A recombinant DNA segment as claimed in claim 3, wherein said plasmid is pBTM126.

5. A recombinant DNA segment as claimed in claim 1, which is pBTM128.

6. A recombinant DNA segment as claimed in claim 1, which is pBTM134.

7. A recombinant DNA segment as claimed in claim 1, which further includes an SD sequence-containing polynucleotide located downstream of said base sequence or said portion thereof, and a peptide-encoding polynucleotide located downstream of said SD sequence-containing nucleotide.

8. A recombinant DNA segment as claimed in claim 7, wherein said SD sequence-containing polynucleotide is a chemically synthesized oligonucleotide.

9. A recombinant DNA segment as claimed in claim 8, wherein said oligonucleotide has a restriction enzyme recognition site downstream from said SD sequence.

10. A recombinant DNA segment as claimed in claim 7, wherein the peptide-encoding polynucleotide is a gene or portion thereof selected from the group consisting of the genes or portions thereof which encode immune interferon, hepatitis B virus surface antigen, hepatitis B virus core antigen, immunoglobulin E, human growth factor and interleukin-2.

11. A recombinant DNA segment as claimed in claim 7, wherein said peptide is human immune interferon.

12. A recombinant DNA segment as claimed in claim 7, wherein said peptide is human interleukin-2.

13. A recombinant DNA segment as claimed in claim 1, which is plasmid pILT-B101 or pHIT-B101.

14. A method of producing a vector, comprising inserting a DNA fragment containing the base sequence depicted in FIG. 1 or a portion thereof which has promoter activity into a vector.

15. A method as claimed in claim 14, wherein said DNA fragment contains the base sequence depicted in FIG. 1.

16. A method as claimed in claim 14, wherein said DNA fragment is obtained from chromosomal DNA of a strain of microorganism belonging to the genus Bacillus.

17. A method as claimed in claim 16, wherein said DNA fragment is obtained from said chromosomal DNA using a promoter cloning vector as said vector.

18. A method as claimed in claim 17, wherein said promoter cloning vector is a plasmid having a restriction enzyme cleavage site in which said DNA fragment can be inserted and permitting the detection of the presence of said DNA fragment inserted thereinto.

19. A method as claimed in claim 18, wherein said plasmid contains no promoters.

20. A method as claimed in claim 18, wherein said plasmid is pBTM126.

21. A method as claimed in claim 17, which further comprises introducing an SD sequence-containing polynucleotide downstream of said DNA fragment into the restriction enzyme cleavage site of said vector.

22. A method as claimed in claim 21, which further comprises introducing a peptide-encoding polynucleotide downstream of said SD sequence-containing polynucleotide.

23. A method as claimed in claim 22, wherein said peptide is human immune interferon.

24. A method as claimed in claim 22, wherein said peptide is human interleukin-2.

25. A transformant of a strain of microorganism belonging to the genus Bacillus transformed with a recombinant DNA according to claim 1.

26. A transformant as claimed in claim 25, which is *Bacillus subtilis* MI114/pILT-B101.

27. A transformant as claimed in claim 25, which is *Bacillus subtilis* MI114/pHIT-B101.

28. A method of producing a transformant of Bacillus, comprising introducing a recombinant DNA segment according to claim 1 into a host organism belonging to the genus Bacillus.

29. A process for the production of a peptide, comprising the steps of:
cultivating a transformant obtained by transforming a strain of microorganism belonging to the genus Bacillus with a vector containing (a) the base sequence depicted in FIG. 1 or a portion thereof which has promoter activity and (b) a peptide-encoding polynucleotide specific for the peptide and located downstream from polynucleotide (a) under conditions which permit the accumulation of the peptide in the culture; and
recovering the peptide from the culture.

30. A process as claimed in claim 29, wherein said transformant is *Bacillus subtilis* MI114/pILT-B101 and said peptide is human interleukin-2.

31. A process as claimed in claim 29, wherein said transformant is *Bacillus subtillis* MI114/pHIT-B101 and said peptide is human immune interferon as the product.

* * * * *